(12) United States Patent
Neilson

(10) Patent No.: US 6,238,350 B1
(45) Date of Patent: May 29, 2001

(54) METHOD OF ANALYZING A CARDIAC SIGNAL

(75) Inventor: James McEwan McIntyre Neilson, Edinburgh (GB)

(73) Assignee: Reynolds Medical Limited, Hertfordshire (GB)

( * ) Notice: Subject to any disclaimer, the term of this patent is extended or adjusted under 35 U.S.C. 154(b) by 0 days.

(21) Appl. No.: 09/367,367

(22) PCT Filed: Mar. 12, 1998

(86) PCT No.: PCT/GB98/00742

§ 371 Date: Aug. 11, 1999

§ 102(e) Date: Aug. 11, 1999

(87) PCT Pub. No.: WO98/40011

PCT Pub. Date: Sep. 17, 1998

(30) Foreign Application Priority Data

Mar. 12, 1997 (GB) .................................................. 9705084
Sep. 17, 1997 (GB) .................................................. 9719740

(51) Int. Cl.[7] .................................................. A61B 5/0452
(52) U.S. Cl. .................................................. 600/508
(58) Field of Search .................................. 600/515, 516, 600/517, 518, 519, 509

(56) References Cited

U.S. PATENT DOCUMENTS 5,419,338    5/1995   Sarma et al. .

FOREIGN PATENT DOCUMENTS 35 36 613 A1    4/1987   (DE) .
WO 95/15116    6/1995   (WO) .

OTHER PUBLICATIONS

J. V. Levert et al., "The relation between QT intervals and heart rate in young healthy males using an incremental head–up tilt protocol", in IEEE conference on computers in cardiology 1996, pp 285–288, Sep. 8–11, 1996, Indianapolis.

C. Funck–Bretano et al., "Rate–corrected QT interval: techniques and limitations", in Am. J. Cardiol., 72:pp17B–22B 1993.

*Primary Examiner*—Scott M. Getzow
(74) *Attorney, Agent, or Firm*—Howson & Howson

(57) ABSTRACT

A method for analyzing a cardiac signal, e.g. an electrocardiogram signal, comprises continuously generating values RR(t) and QT(t), representing the RR and QT intervals respectively as functions of time, and operating on one or both values to compensate for the naturally occurring delay between the change in the RR interval and the resulting change in the QT interval. A delay may be introduced into the RR(t) value by a resistor-capacitor network having two time constants $T_1$ and $T_2$. After compensating for the delay, S(t), the slope of the graph of the QT interval against the RR interval may be found and used to generate Qtc(t), the corrected QT interval at a standard RR interval. Alternatively, an advance may be introduced into the value QT(t). Apparatus for generating Qtc(t) may include a hybrid digital/analog circuit applying an "xth root law."

54 Claims, 6 Drawing Sheets

METHOD OF ANALYZING A CARDIAC SIGNAL

FIELD OF THE INVENTION

The present invention relates to a method of analysing a cardiac signal.

Each beat of the heart generates a sequence of electrical waves called an "ecg (electrocardiogram) complex", which can be monitored and recorded by apparatus such as an electrocardiograph connected to the body by a set of electrodes attached to the skin. Within each complex separate waves traditionally labelled P,Q,R,S and T are recognised as shown in FIG. 1.

The interval between one heart beat and the next can be measured between corresponding waves in successive complexes, usually that between the R waves and hence is usually referred to as the "RR interval". Within each complex itself, other intervals can be considered, particularly the "QT interval" from the start of the Q wave to the end of the T wave.

In the course of the day the heart rate varies in response to the demands of the body and this is reflected in constant variation of the RR interval. As the heart rate increases and the RR interval shortens so, to maintain stable conditions within the heart, the QT interval shortens in sympathy and lengthens again as the heart slows and the RR Interval increases.

Because the maintenance of an appropriate balance between RR and QT interval durations is thought to be important in avoiding serious disturbance of the heart rhythm and possible Cardiac Arrest, there is considerable medico-scientific interest in studying the relationship between RR and QT intervals as the heart rate varies throughout the day in response to therapy.

The importance of this relationship stems from its use to estimate from the QT and RR intervals pertaining at the time a patient's ecg was observed, what the QT interval would be at a "standard" RR interval of 1.0 seconds (the so called "corrected" QT interval, "QTc"). From this measure it can be considered whether the patient's QT interval is "normal" or not.

To define this relationship many workers have measured RR intervals and the corresponding QT intervals from ecg complexes obtained from a given individual at different times of the day to obtain data covering a range of RR intervals. These pairs of values are then plotted as points on a graph of QT vs RR such as that shown in FIG. 2. From the scatter of experimental points so obtained different workers have used statistical techniques to fit the "best" curves to their particular collections of data so as to obtain empirical "laws" from which to predict the QTc interval corresponding to the QT interval observed at a particular RR interval, RRc.

As early as 1920 Dr Bazett declared that for the population of normal individuals a square root formula of the type QT=QTc√(RR/RRc) best fitted his data (Curve (a) in FIG. 2). Others suggested a cube root formula QT=QTc $\sqrt[3]{}$ (RR/RRc) (Curve (b)), while still others have advocated a linear approximation QT=QTc+s (RR−RRc) (Curve (c)) where s is the slope of the line.

Whichever formula is selected to represent the "law" relating QT and RR intervals, it can then be used to estimate the "heart rate corrected" value of QT, namely QTc, from the chosen formula, viz:

$$QTc = \frac{QT}{(RR/RRc)^{1/2}} \ldots \text{Bazett square root formula}$$

or $$QTc = \frac{QT}{(RR/RRc)^{1/3}} \ldots \text{Cube root formula}$$

or $$QTc = \frac{QT}{(RR/RRc)^{x}} \ldots \text{An "xth root" formula}$$

or

QTc=QT−s. (RR−RRc)        using the linear formula

By long familiarity and decades of usage, despite frequent criticism of its inaccuracies the square root Bazett "law" is usually assumed, and "corrected" (QTc) intervals calculated to demonstrate that an individual's QT interval has been affected by influences other than heart rate (RR interval) with the passage of time or change in the individual's physical condition or health.

Since the standard RR interval, RRc, is already chosen (1.0 seconds), QTc can be calculated immediately from the observed values of QT, RR, and either s (linear formula), or "x", be it equal to ½ (square root formula), or ⅓ (cube root formula) or any other value.

Apparatus (herein referred to as a "Basic QT Analyser") already exists which can accept a continuous ecg signal detect the ecg complexes, identify the component waves and measure the RR intervals and the QT intervals in each complex, thus generating a continuous stream of successive RR intervals each accompanied by its associated QT interval.

These intervals can be output from such analysing apparatus either in digital form as a sequence of coded numbers, or in analogue form as time varying voltage signals representing the RR intervals as the time function RR(t) and the QT intervals as the time function QT(t).

A complication stands in the way of analysis of the relationship between the ever changing RR interval and the QT interval response. It is found that the QT response to a change in RR(t) is subject to a time delay or "QT lag" which is not fixed but depends on the time course of the change in RR(t). This frustrates the estimation of s, the rate of change of QT(t) with change of RR(t).

SUMMARY OF THE INVENTION

From a first aspect, the present invention provides a method of analysing a cardiac signal, comprising continuously or continually generating values RR(t) and QT(t) representing the RR and QT intervals respectively as functions of time, and operating on one or both of said values so as to compensate for the delay between the change in RR interval and the resulting change in QT interval, to produce output values R(t) and Q(t) respectively. A delay may be introduced into the RR(t) value or an advance introduced into the QT(t) value. The values R(t) and Q(t) may be generated either as analogue electrical signals or as discrete numerical values.

Conveniently, the delay or advance to be introduced is modelled by means of a resistor-capacitor network and preferably the network is adjustable. In a preferred embodiment the resistor-capacitor network has two different time constants which are applied in an adjustable ratio.

From a second aspect, the present invention provides a method of analysing a cardiac signal, comprising continuously generating values R(t) and Q(t) representing the RR and QT intervals respectively as functions of time, and continuously generating S(t), the time function of the slope of the graph of QT interval against RR interval, by operating on the continuously generated values R(t) and Q(t).

The method may include the steps of continuously generating values of $\Delta Q(t)$ and $\Delta R(t)$, respectively representing the change in the value of Q(t) and R(t) over a time interval $\Delta t$, and continuously determining the quotient $\Delta Q(t)/\Delta R(t) = S(t)$.

Preferably, however, the method includes the step of cross-correlating the values R(t) and Q(t) to determine S(t). In a particular embodiment, the running average of a regression coefficient S is determined over a moving window of a given duration. Optionally, the running average of a correlation coefficient r is also determined.

The signal S(t) then represents the ever changing slope of the QT(t)/RR(t) relationship, freed from the effects of QT lag because of the compensated Q(t) or R(t) function.

Using this method, at every point in time throughout the continuous analysis, a set of three corresponding values R(t), Q(t) and S(t) is available. In order to give a continuous determination of QTc(t), the time function of the corrected QT interval, the method preferably includes the steps of selecting a formula which is assumed to relate QTc(t) to R(t), the "standard" RR interval RRc, Q(t) and S(t) and continuously generating values of QTc(t) by applying the selected formula. If a linear "law" is assumed, the formula will be $$QTc(t) = Q(t) + S(t)[RRc - R(t)]$$

Alternatively, if an "xth root law" is assumed, the actual value of x can be continuously calculated from the data itself:

$$x(t) = S(t)[R(t)/Q(t)]$$

and the formula applied to determine QTc(t) is $$QTc(t) = \frac{Q(t)}{(R(t)/RRc)^{x(t)}}$$

The method of the invention can be performed in real time. Preferably, however, ecg data is accumulated over a statistically significant period and is then processed by the method of the invention. For example, ecg data can be stored on magnetic tape for a 24 hour period and then processed at high speed, for example in 90 seconds.

From a third aspect, the present invention provides apparatus for analysing a cardiac signal in real time, comprising means for continuously or continually monitoring values RR(t) and QT(t) representing the RR and QT intervals respectively as functions of time, and means for compensating for the delay between the change in RR interval and the resulting change in QT interval to produce output values R(t) and Q(t) respectively.

The compensating means may comprise means for introducing a delay into the RR(t), value or means for introducing an advance into the QT(t) value. In an embodiment of the invention in which the values of RR(t) and QT(t) are represented by analogue electrical signals, the means for introducing a delay or an advance may comprise a resistor-capacitor network which is preferably adjustable. The resistor-capacitor network preferably has two different time constants which can be applied in an adjustable ratio.

From a fourth aspect, the invention provides apparatus for analysing a cardiac signal, comprising means for continuously monitoring values R(t) and Q(t) representing the RR and QT intervals respectively as functions of time, and means for continuously determining therefrom the value of S(t) representing the slope of the graph of QT interval against RR interval.

The apparatus may comprise means for continuously generating values of $\Delta Q(t)$ and $\Delta R(t)$, respectively representing the change in the value of Q(t) and R(t) over a time interval $\Delta t$, and means for determinating the value of S(t) from the quotient $\Delta Q(t)/\Delta R(t)$.

The means for generating $\Delta R(t)$ and $\Delta Q(t)$ may comprise electronic differentiator circuits and the means for determining the quotient may comprise an electronic divider circuit.

Preferably, however, the apparatus comprises means for cross-correlating the values of R(t) and Q(t) to determine S(t). The cross-correlating means may include averaging circuits, multiplying circuits and a circuit for extracting a square root.

Preferably, the apparatus includes means for setting a value representing RRc, a standard RR interval, and means for applying a selected formula involving R(t), RRc, Q(t) and S(t) in order to generate continuously or continually a value representing QTc(t), the time function of the corrected QT interval.

The means for setting the value representing RRc may comprise an adjustable voltage divider. If a linear relationship for QTc(t) is assumed, the formula-applying means may comprise means for subtracting the R(t) signal from the RRc value, means for multiplying this difference by the S(t) signal and means for adding the product to the Q(t) signal.

Alternatively, if an "xth root law" is assumed, the apparatus preferably includes means for continuously generating a value of x(t), the time function of x. This may comprise a divider circuit which divides the R(t) signal by the Q(t) signal and a multiplying circuit which multiplies the quotient R(t)/Q(t) by the S(t) signal. The formula-applying means may then comprise a Read Only Memory to which digital values of signals representing R(t)/RRc and x(t) are applied, and which outputs digital values representing $(R(t)/RRc)^{x(t)}$, to a digital-to-analogue converter for converting said output values to an analogue signal, and a divider circuit for dividing the Q(t) signal by the output analogue signal, to obtain a signal representing QTc(t).

As an alternative to the analogue or hybrid analogue/digital circuits mentioned above, the apparatus may utilize digitised values instead of the analogue R(t) and Q(t) signals, and may comprise logic gates and Read Only Memories for effecting the method steps.

The present invention will now be described in more detail, by way of example only, with reference to the accompanying drawings, in which:

DETAILED DESCRIPTION

The circuits of FIGS. 3a to 6 perform analogue operations on the signals RR(t) and QT(t) which are obtained using an analogue Basic QT Analyser (not shown in the Figures). As a preliminary step, these signals are smoothed to remove noise in a conventional manner, using two identical smoothing circuits.

Figure 1:
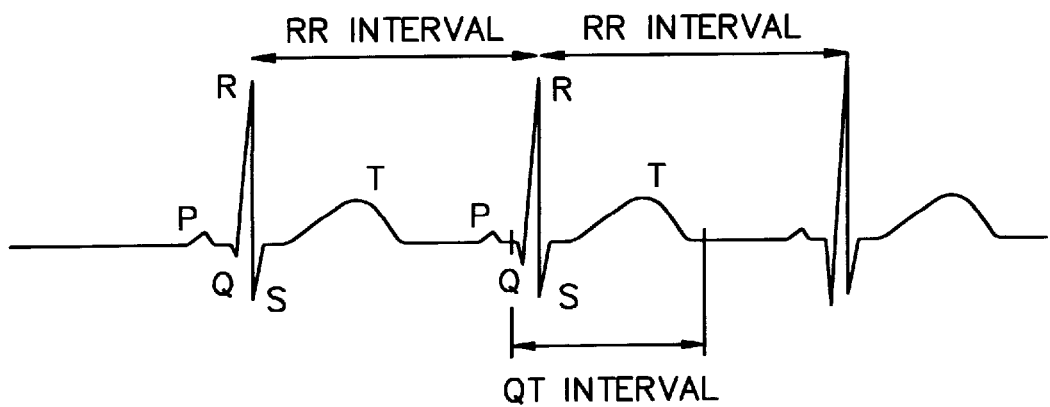
FIG. 1 shows ecg complexes of a cardiac signal.
Figure 2:
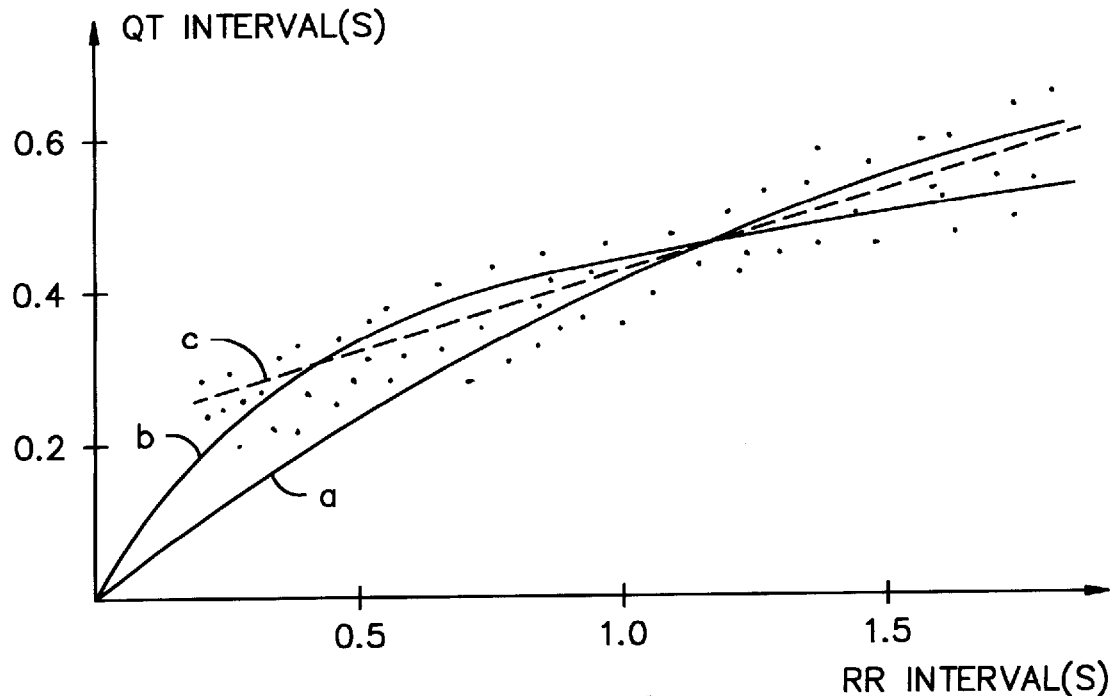
FIG. 2 is a graph showing curves of possible empirical formulae for relating the QT and RR intervals.
Figure 3A:
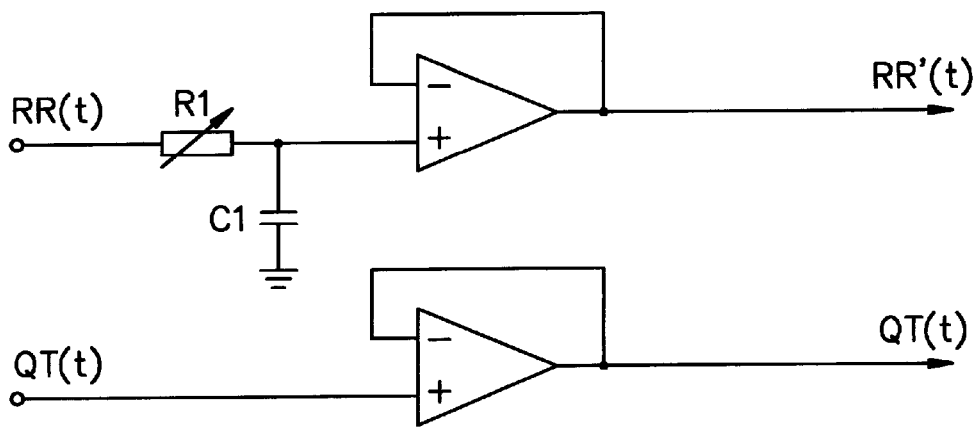
FIGS. 3a and 3b show electronic circuits for introducing a delay into the RR(t) signal, according to embodiments of the invention.

FIG. 3a shows a circuit in which the time lag by which changes in the QT interval follow changes in the RR interval is modelled as that imposed on an electrical signal by a network comprising an adjustable resistor R1 and a capacitor C1. The buffered output RR'(t) represents the RR(t) signal delayed by the identical time lag suffered by the real QT(t) signal. Thus the "QT lag" has been eliminated and there is no relative time lag between the signals RR'(t) and QT(t).

Figure 3B:
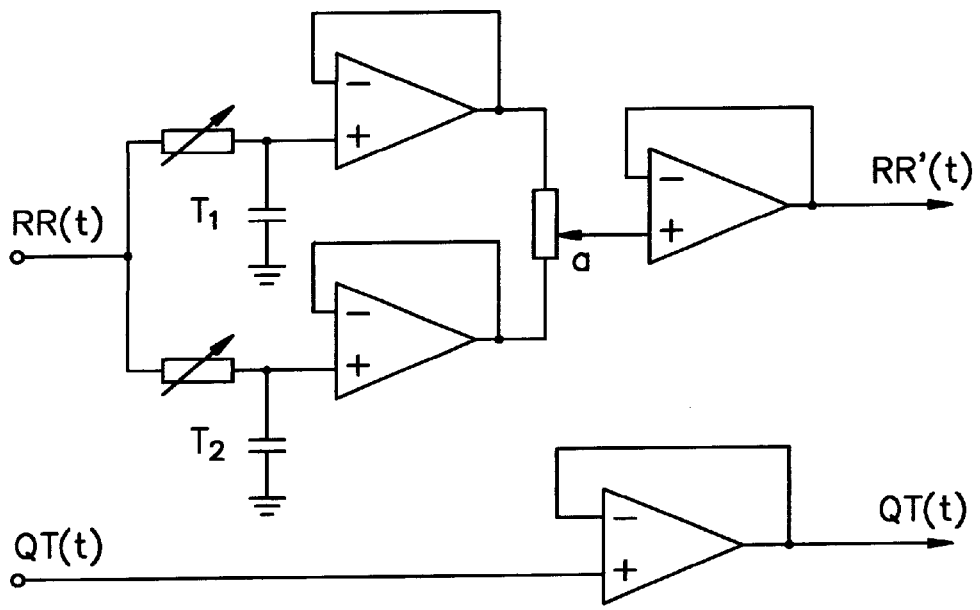

FIG. 3b shows a more versatile alternative compensation network, combining first and second RC circuits having different time constants $T_1$, $T_2$ respectively. The overall time lag can be adjusted towards $T_1$, or towards $T_2$ using a potentiometer set at a position a.

When the "QT lag" is modelled using this network, the response RR'(t) of the network to an input waveform representing the time course of RR(t) is found to have the same waveform as the actual QT(t) waveform which accompanied the RR(t) except for a constant of proportionality representing the sensitivity S or rate of change of QT with RR.

More formally using the Laplace transform variable p, the relationship between RR'(t) and RR(t) has the transfer function:

$$RR'(p)=RR(p) [a/(1+pT_1)+(1-a)/(1+pT_2)]$$

where the two time constants are $T_1$ and $T_2$ and the factor a determines the proportions in which the two lagging responses are added.

In the human heart, the sensitivity of QT(t) change to change in RR(t) in the steady state (the slope of the QT/RR characteristic) is S so that the change of QT(t) with time in response to a change in RR(t) with time reflects the underlying sensitivity S but modified by the "QT lag" depending on the time course of the RR(t) change. Thus, for a very slow change in RR(t) over a time which is long compared with time constants $T_A$ and $T_B$, which are two time constants governing the "QT lag" when applied together in a ratio $\alpha:(1-\alpha)$, with $0<\alpha<1$, $$dQT(t)/dt=S.dRR(t)/dt$$

For faster changes over times comparable to $T_A$ or $T_B$, dQT(t)/dt will be equal to S.dRR(t)/dt but modified by the double time constant "QT lag".

Taking Laplace transforms then:

$$LdQT(t)/dt=pQT(p)=p.S.RR(p). [\alpha/(1+pT_A)+(1-\alpha)/(1+pT_B)]$$

Returning now to the double time constant RC network of FIG. 3b which attempts to simulate the naturally occurring "QT lag" using lagging time constants $T_1$ and $T_2$, the lagging responses being added in a proportion determined by the factor a, the output of this network is RR'(t) and the transform of RR'(t) is RR'(p)

$$\text{where } RR'(p)=RR(p). [a/(1+pT_1)+(1-a)/(1+pT_2)]$$

Differentiating this we obtain dRR'(t)/dt, the transform of which is:

$$LdRR'(t)/dt=p.RR'(p)=p.RR(p). [a/(1+pT_1)+(1-a)/(1+pT_2)]$$

Now dividing dQT(t)/dt by dRR'(t)/dt we obtain:

$$[dQT(t)/dt]/[dRR'(t)/dt] = \frac{SL^{-1}(p \cdot RR(p)[\alpha/(1+pT_A)+(1-\alpha)/(1+pT_B)])}{L^{-1}(p \cdot RR(p)[a/(1+pT_1)+(1-a)/(1+pT_2)])}$$

If we adjust the circuit such that $T_1=T_A$, $T_2=T_B$ and $a=\alpha$, then $$[dQT(t)/dt]/[dRR'(t)/dt]=S$$

The above equation for S is independent of and applies for all RR(t), that is, for any waveform of RR change so long as $T_1$, $T_2$ and a are correctly adjusted to equal $T_A$, $T_B$ and $\alpha$.

It has been found that $T_1=0$; $T_2=60$ s and a=0.33 gives good compensation for QT lag across a wide range of electrocardiograms from sick patients and normal subjects so that these settings can be preset in the apparatus and no subsequent adjustment is normally necessary.

Figure 4:
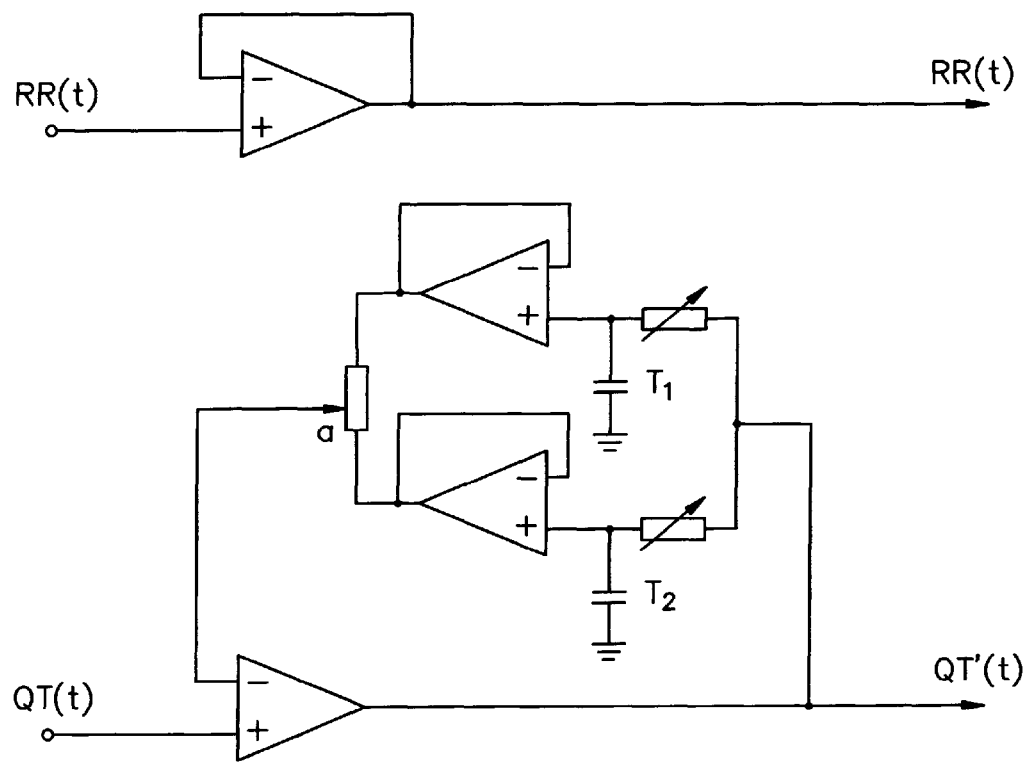
FIG. 4 shows an electronic circuit for introducing an advance into the QT(t) signal.

FIG. 4 shows a further alternative circuit for compensating for "QT Lag". The smoothed RR(t) signal is left unaltered, except for buffering, and the smoothed QT(t) signal is passed through a circuit comprising the RC circuits of FIG. 3b, but incorporated into a feedback path of an operational amplifier to have the effect of advancing the signal rather than delaying it. The compensated QT(t) signal is designated QT'(t).

If the circuit of FIG. 3a or 3b is used, the signal RR'(t) becomes R(t) and the signal QT(t) becomes Q(t). If the circuit of FIG. 4 is used, RR(t) becomes R(t) and QT'(t) becomes Q(t). In either event, R(t) and Q(t) are two continuously generated signals from which the time lag between the basic signals RR(t) and QT(t) has been eliminated.

Figure 5:
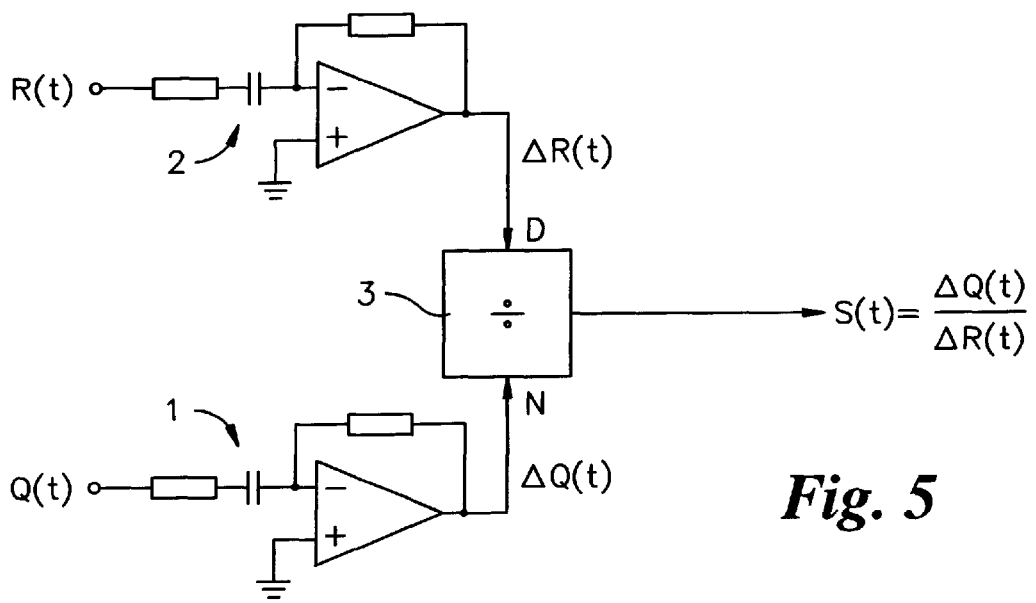
FIG. 5 shows a circuit for deriving the S(t) signal.

FIG. 5 shows a circuit for generating S(t), the slope of the Q(t)/R(t) relationship. Identical differentiator circuits 1,2 are used to generate signals ΔQ(t) and ΔR(t) from the Q(t) and R(t) signals respectively. The ΔQ(t) signal represents the change in Q(t) and the ΔR(t) signal represents the change in R(t), over a suitable time interval Δt. As an alternative to the differentiator circuits 1, 2, a.c. coupling or high pass filter circuits could be used. An analogue divider circuit 3 is then used to continuously generate the quotient ΔQ(t)/ΔR(t)=S(t).

Figure 6:
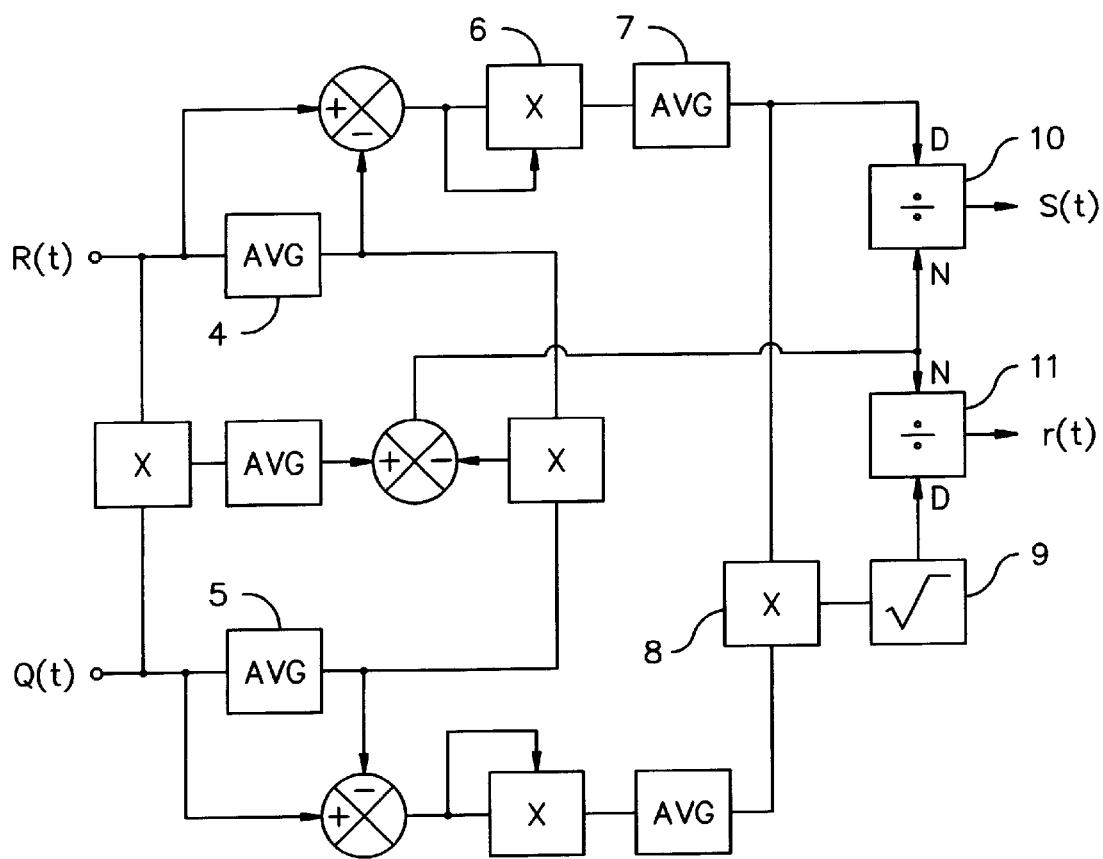
FIG. 6 shows an alternative circuit for deriving the S(t) signal by cross-correlation.

FIG. 6 shows an alternative circuit for generating S(t) from the compensated signals R(t) and Q(t). These signals are applied to electronic averaging circuits 4, 5 respectively, the output of the averaging circuits being a continuously generated equivalent to the time average, over a selected time interval T, of the input signal. Thus for example the output of the averaging circuit 4 is $$\frac{1}{T}\int_{(t-\frac{T}{2})}^{(t+\frac{T}{2})} R(t)dt$$

which is designated $\overline{R(t)}$, and the output from the averaging circuit 5 is $\overline{Q(t)}$. The averaging circuits may range in complexity from simple low pass smoothing filters to more complex transversal filters with equally weighted taps.

The signal $\overline{R(t)}$ is subtracted from $R(t)$ and the result is squared at an electronic multiplier circuit 6 to give $[R(t)-\overline{R(t)}]^2$. This signal is then time averaged by an averaging circuit 7 to give $\overline{[R(t)-\overline{R(t)}]^2}$. Similar processing is performed on the $Q(t)$ signal to generate $\overline{[Q(t)-\overline{Q(t)}]^2}$. The two generated signals are multiplied by a multiplying circuit 8, the output of which is applied to a square root extracting circuit 9. Meanwhile, the product of the $R(t)$ and $Q(t)$ signals is processed to generate $\overline{R(t)Q(t)}-\overline{R(t)}\cdot\overline{Q(t)}$. Two quadrant analogue divider circuits 10 and 11 are used to generate $S(t)$ the regression coefficient and $r(t)$, the cross-correlation coefficient, respectively, where $$S(t) = \frac{\overline{R(t)Q(t)} - \overline{R(t)} \cdot \overline{Q(t)}}{\overline{[R(t) - \overline{R(t)}]^2}} \text{ and}$$

$$r(t) = \frac{\overline{R(t)Q(t)} - \overline{R(t)} \cdot \overline{Q(t)}}{\sqrt{\overline{[R(t) - \overline{R(t)}]^2} \cdot \overline{[Q(t) - \overline{Q(t)}]^2}}}$$

The cross correlation technique of FIG. 6 is particularly advantageous. Additionally, the cross-correlation coefficient $r(t)$ can be used to "gate" the output of $S(t)$ so that the latter is only passed to the rest of the system when $r(t)$ is greater than a predetermined limit such as 0.8. This indicates that the accuracy of the slope signal $S(t)$ has been relatively little affected by noise and can be accepted with greater confidence.

At this stage in the process, a continuous trend record can be generated, showing $R(t)$, $Q(t)$ and $S(t)$, plotted against time.

Figure 7:
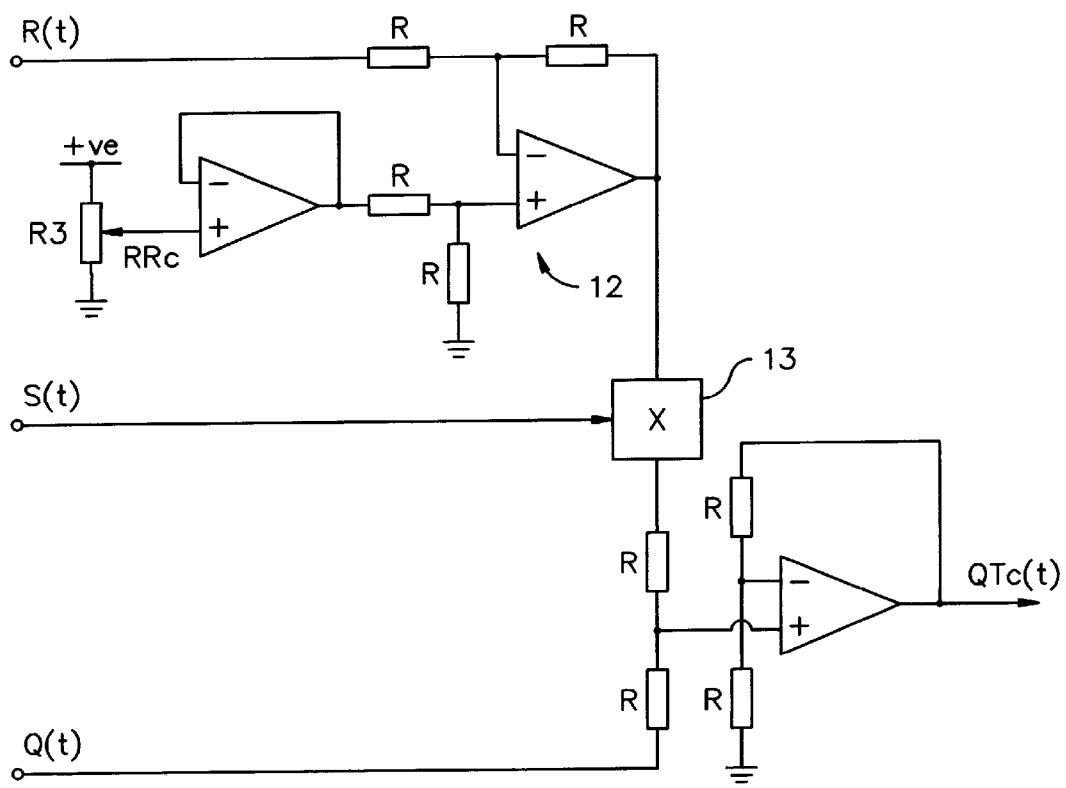
FIG. 7 shows a circuit for obtaining the QTc(t) signal, assuming a "linear law"

FIG. 7 shows a circuit for generating the time function signal of the corrected QT interval, QTc(t), assuming a linear relationship between QT and RR. Firstly the circuit of FIG. 5 or 6 is used to generate $S(t)$.

A voltage divider comprising a potentiometer R3 is used to set the desired value of an RRc signal representing the duration of the standard RR interval, and the $R(t)$ signal is then subtracted from the RRc signal using a subtracter circuit 12. The resulting signal, RRc–$R(t)$, is applied to one input of a multiplier circuit 13 which takes its other input from the $S(t)$ signal. The product $S(t)$ [RRc–$R(t)$] is then added to the signal $Q(t)$ to give the continuous estimation of QTc(t).

Figure 8:
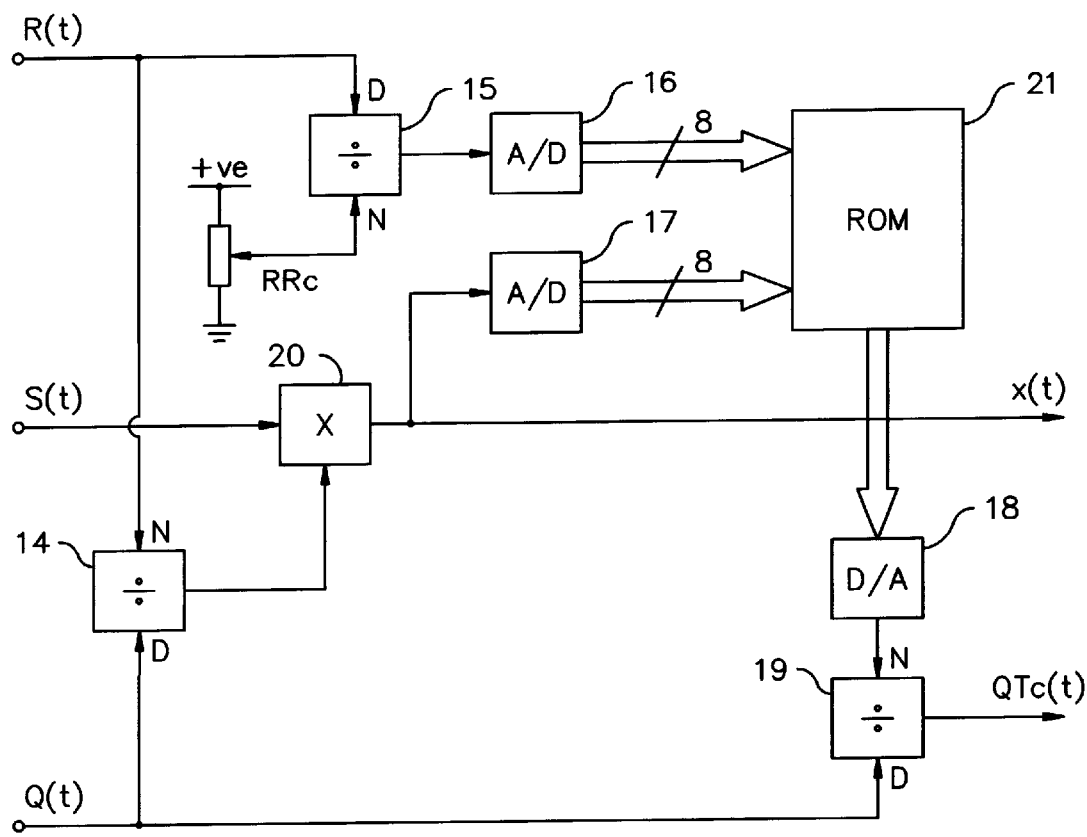
FIG. 8 shows a circuit for obtaining the QTc(t) signal, assuming an "xth root law".

FIG. 8 shows a hybrid digital/analogue analyser which is used to determine QTc(t) assuming that an "xth root law" holds.

An analogue divider 14 generates the quotient $R(t)/Q(t)$, which is then multiplied by $S(t)$, using a multiplier 20, to produce the function $x(t)$.

The value of $R(t)/RRc$ is found using an analogue divider 15 comprising an adjustable resistor R4 which is set to provide a voltage corresponding to the value of RRc. The signals $R(t)/RRc$ and $x(t)$ are converted to 8 bit digital signals using respective analogue-to-digital converters 16,17. These signals are applied to the address inputs of a Read Only Memory 21, which constitutes a "look-up table" continually reading out values for $(R(t)/RRc)^{x(t)}$ as 8 bit digital signals. A digital-to-analogue converter 18 then converts these signals back to an analogue signal. The required signal QTc(t) is generated by an analogue divider 19, which divides the $Q(t)$ signal by the output from converter 18.

The method of QT/RR analysis described has been in use in the inventors' laboratory for months and many 24 hour ecg's have been analysed showing that S, x, and QTc all vary significantly throughout the day. For example the value of x has been seen to vary from less than 0.2 to nearly 1.0 in the same patient during a single day illustrating the futility of the long running controversy over whether x=0.5 or x=0.33. The answer is it is both and neither as it varies over the hours. Both the Slope S and QTc are seen to vary considerably and it seems likely that sinister combinations of these variables may sometimes arise and usher in serious rhythm disturbances.

It will be appreciated that the method allows moment by moment determination of which of the possible and wide ranging QT/RR characteristic curves applies and that this involves first estimating the Slope S and hence the exponent x, which in turn requires that the QT lag is compensated.

Digital equipment could be used as an alternative to the analogue circuits that have been described. For example, electronic logic gates and fuse-link Read Only Memories (ROMS) could be interconnected so as to perform the sequence of operations described when triggered by successive clock pulses. Such pre-programmed or "pre-wired" digital apparatus would derive from ecg signals the time course of the $R(t)$, $Q(t)$, $S(t)$, $x(t)$ and QTc(t) signals. It will also be apparent that the method of the present invention can be executed by a general purpose digital computer or microprocessor when programmed with software specifying the operations required to simulate the actions of the pre-wired digital analyser.

What is claimed is:

1. A method of analysing a cardiac signal, comprising continuously or continually generating values RR(t) and QT(t) representing the RR and QT intervals respectively as functions of time, and operating on one or both of said values so as to compensate for the delay between the change in RR intervals and the resulting change in QT interval, to produce output values $R(t)$ and $Q(t)$ respectively.

2. A method according to claim 1, comprising introducing a delay into the value RR(t) to produce a compensated output value $R(t)$.

3. A method according to claim 1, comprising introducing an advance into the value QT(t) to produce a compensated output value $Q(t)$.

4. A method according to claim 2, wherein the output values are generated as analog electrical signals.

5. A method according to claim 4, wherein the delay or advance to be introduced is modeled by means of a resistor capacitor network.

6. A method according to claim 2, wherein said delay or advance comprises two different time constants.

7. A method according to claim 6, wherein a first of said time constants is approximately zero.

8. A method according to claim 6, wherein a second of said time constants is approximately 60 s.

9. A method according to claim 6, wherein a first of said time constants is approximately zero, a second of said time constants is approximately 60 s, and said first and second time constants are applied to the value to be delayed in a ratio of approximately 1:2.

10. A method according to claim 6 comprising applying said two different time constants to the RR(t) value in an adjustable ratio.

11. A method analyzing a cardiac signal according to claim 1, comprising continuously or continually generating $S(t)$, the time function of the slope of the graph of QT interval against RR interval, by operating on the output values $R(t)$ and $Q(t)$.

12. A method of analyzing a cardiac signal, comprising continuously or continually generating values $R(t)$ and $Q(t)$ representing the RR and QT intervals respectively as functions of time, and continuously or continually generating S(t), the time function of the slope of the graph of the QT interval against the RR interval, by cross-correlating the values R(t) and Q(t), wherein the running average of a regression coefficient is determined over a moving window of given duration.

13. A method according to claim 12, wherein the running average of a correlation coefficient r is also determined.

14. A method of analyzing a cardiac signal, comprising continuously or continually generating values R(t) and Q(t) representing the RR and QT intervals respectively as functions of time, and continuously or continually generating S(t), the time function of the slope of the graph of the QT interval against the RR interval by operating on the values R(t) and Q(t), and comprising a further step of continuously or continually determining QTc(t), the time function of the QT interval at a standard RR interval RRc, by selecting a formula which is assumed to relate QTc(t) to R(t), Q(t), S(t) and RRc, and continuously or continually generating a value of QTc(t) by applying the selected formula.

15. A method according to claim 14, wherein the formula is

QTc(t)=Q(t)+S(t) {RRC−R(t)}.

16. A method according to claim 14, wherein the formula is $$QTc(t) = \frac{Q(t)}{(R(t)/RRc)^{x(t)}},$$

where x(t)=S(t) {R(t)/Q(t)}.

17. Apparatus for analyzing a cardiac signal, comprising means for continuously or continually monitoring value RR(t) and QT(t) representing the RR and QT intervals respectively as functions of time, and means for compensating for the delay between the change in RR interval and the resulting change in QT interval, to produce output values R(t) and Q(t) respectively.

18. Apparatus according to claim 17, comprising means for introducing a delay into the value RR(t).

19. Apparatus according to claim 17, comprising means for introducing an advance into the value QT(t).

20. Apparatus according to claim 18, for use when the values RR(t) and QT(t) are represented by analog electrical signals, wherein the means for introducing a delay comprises a resistor-capacitor network.

21. Apparatus according to claim 20, wherein said resistor-capacitor network has a single, adjustable time constant.

22. Apparatus according to claim 20, wherein said resistor-capacitor network has two time constants.

23. Apparatus according to claim 22, wherein at least one of said time constants is adjustable.

24. Apparatus according to claim 22, wherein a first of said time constants is present at approximately zero.

25. Apparatus according to claim 24, wherein a second of said time constants is preset at approximately 60 s.

26. Apparatus according to claim 25, wherein said first and second time constants are applied to the value to be delayed in a ratio of approximately 1:2.

27. Apparatus according to claim 22, comprising an adjustable voltage divider for applying said time constants to the value to be delayed in an adjustable ratio.

28. Apparatus for analyzing a cardiac signal according to claim 17, comprising means for continuously or continually determining, from the output values R(t) and Q(t), the value of S(t) representing the slope of the graph of QT interval against RR interval.

29. Apparatus for analyzing a cardiac signal, comprising means for continuously or continually monitoring values R(t) and Q(t) representing the RR and QT intervals respectively as functions of time, and means for continuously or continually cross-correlating the values of R(t) and Q(t) to determine the value of S(t), representing the slope of the graph of the QT interval against the RR interval.

30. Apparatus according to claim 29, wherein the cross-correlating means comprise means for finding the average of the product R(t) Q(t) over a given time period, means for finding the product of the averages of R(t) and Q(t) over the same time period, means for subtracting said product of the averages from said average of the product to obtain a numerator, means for squaring the difference between R(t) and the average of R(t) over the given time period, means for averaging the square of the difference over said time period to obtain a denominator, and means for dividing the numerator by the denominator to obtain S(t).

31. Apparatus for analyzing a cardiac signal, comprising means for continuously or continually monitoring values R(t) and Q(t) representing the RR and QT intervals respectively as functions of time, and means for continuously or continually determining therefrom the value of S(t), representing the slope of the graph of the QT interval against the RR interval by operating on the values R(t) and Q(t), including means for setting a value RRc, representing a standard RR interval, and means for applying a selected formula involving R(t), RRc, Q(t) and S(t) in order to continuously or continually generate a value representing QTc(t), the time function of the corrected QT interval.

32. Apparatus according to claim 31, wherein the means for setting RRc comprises an adjustable voltage divider.

33. Apparatus according to claim 31, comprising means for subtracting the R(t) value from the RRc value, means for multiplying the resulting difference by the S(t) value, and means for adding the product to the Q(t) value to generate the value of QTc(t).

34. Apparatus according to claim 31, comprising means for finding the quotient R(t)/RRc, means for raising the quotient to a power to obtain a denominator, and means for dividing the Q(t) value by the denominator to generate the value of QTc(t).

35. Apparatus according to claim 34, comprising means for continuously or continually calculating said power, the power calculating means comprising means for dividing the R(t) value by the Q(t) value and means for multiplying the quotient R(t)/Q(t) by the S(t) value.

36. Apparatus according to claim 34, wherein the means for raising the quotient to the power comprises a Read Only Memory in the form of a look-up table.

37. Apparatus according to claim 34, wherein the means for finding the quotient R(t)/RRc and the means for dividing the Q(t) value by the denominator comprise analog divider circuits.

38. A method according to claim 3, wherein the output values are generated as analog electrical signals.

39. A method according to claim 38, wherein the advance to be introduced is modeled by means of a resistor capacitor network.

40. A method according to claim 3, wherein said advance comprises two different time constants.

41. A method according to claim 40, wherein a first of said time constants is approximately zero.

42. A method according to claim 40, wherein a second of said time constants is approximately 60 s.

43. A method according to claim 40, wherein a first of said time constants is approximately zero, a second of said time constants is approximately 60 s, and said first and second time constants are applied to the value to be delayed in a ratio of approximately 1:2.

44. A method according to claim 6 comprising applying said two different time constants to the RR(t) value in an adjustable ratio.

45. Apparatus according to claim 19, for use when the values RR(t) and QT(t) are represented by analog electrical signals, wherein the means for introducing an advance comprises a resistor-capacitor network.

46. Apparatus according to claim 45, wherein said resistor-capacitor network has a single, adjustable time constant.

47. Apparatus according to claim 45, wherein said resistor-capacitor network has two time constants.

48. Apparatus according to claim 47, wherein at least one of said time constants is adjustable.

49. Apparatus according to claim 47, wherein a first of said time constants is present at approximately zero.

50. Apparatus according to claim 49, wherein a second of said time constants is preset at approximately 60 s.

51. Apparatus according to claim 50, wherein said first and second time constants are applied to the value to be advanced in a ratio of approximately 1:2.

52. Apparatus according to claim 47, comprising an adjustable voltage divider for applying said time constants to the value to be advanced in an adjustable ratio.

53. A method according to claim 13, wherein the function S(t) is only accepted when the correlation coefficient r is greater than a predetermined limit.

54. A method according to claim 53, wherein said predetermined limit is 0.8.

* * * * *

UNITED STATES PATENT AND TRADEMARK OFFICE
CERTIFICATE OF CORRECTION

| | | |
|---|---|---|
| PATENT NO. | : 6,238,350 B1 | Page 1 of 1 |
| APPLICATION NO. | : 09/367367 | |
| DATED | : May 29, 2001 | |
| INVENTOR(S) | : James McEwan McIntyre Neilson | |

It is certified that error appears in the above-identified patent and that said Letters Patent is hereby corrected as shown below:

Column 1, after line 6, insert --BACKGROUND OF THE INVENTION--;

Signed and Sealed this

Thirty-first Day of July, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,238,350 B1 | Page 1 of 1 |
| APPLICATION NO. | : 09/367367 | |
| DATED | : May 29, 2001 | |
| INVENTOR(S) | : James McEwan McIntyre Neison | |

It is certified that error appears in the above-identified patent and that said Letters Patent is hereby corrected as shown below:

Column 8, claim 5, lines 44 and 45, delete "or advance";

Column 8, claim 6, lines 47 and 48, delete "or advance".

Signed and Sealed this

Second Day of October, 2007

JON W. DUDAS
*Director of the United States Patent and Trademark Office*